United States Patent [19]

Bandurco et al.

[11] 4,129,653
[45] Dec. 12, 1978

[54] SUBSTITUTED PYRROLO [1,2-C] QUINAZOLINES AND PHARMACEUTICAL COMPOSITIONS AND METHODS EMPLOYING THEM

[75] Inventors: Victor T. Bandurco, Somerville; Seymour Levine, North Brunswick, both of N.J.

[73] Assignee: Ortho Pharmaceutical Corporation, Raritan, N.J.

[21] Appl. No.: 757,117

[22] Filed: Jan. 5, 1977

[51] Int. Cl.$^2$ .................. A61K 31/505; C07D 487/14
[52] U.S. Cl. .................................... 424/251; 544/252; 544/60; 544/115; 424/246; 424/248.56

[58] Field of Search ..... 260/251 A, 251 QA, 256.4 F, 260/256.4 Q, 247.5 DP, 243 B; 424/251, 246, 248.56; 544/55, 60, 252, 96, 115

[56] References Cited

PUBLICATIONS

Ajello, Chemical Abstracts, vol. 77, 152,110p (1972).
Ivin et al, Chemical Abstracts, vol. 72, 111,415v (1970).
Lown et al, Can. J. Chem., vol. 49(8), 1165–1175 (1971).
Beveridge et al., Chemical Abstracts, vol. 72, 111414u (1970).

*Primary Examiner*—Donald G. Daus
*Assistant Examiner*—Diana G. Rivers
*Attorney, Agent, or Firm*—Benjamin F. Lambert

[57] ABSTRACT

Substituted pyrrolo[1,2-c] quinazolines useful for their cardiovascular activities and as antiasthmatic agents.

29 Claims, No Drawings

SUBSTITUTED PYRROLO [1,2-C] QUINAZOLINES AND PHARMACEUTICAL COMPOSITIONS AND METHODS EMPLOYING THEM

BACKGROUND OF THE INVENTION

3-Hydroxy-1,2-diphenylpyrrolo[1,2-c]quinazoline and 1,2-diphenyl-3-ethoxypyrrolo[1,2-c]quinazoline have been reported by J. W. Lown and K. Matsumoto in Can. J. Chem. 49, 1165 (1971).

DESCRIPTION OF THE INVENTION

The present invention relates to novel substituted pyrrolo[1,2-c]quinazolines and more particularly to those having the following formulas:

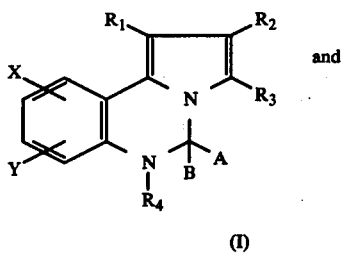

(I)

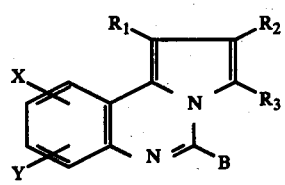

(II)

wherein:

$R_1$ and $R_2$ are each members selected from the group consisting of hydrogen, loweralkyl, loweralkenyl, aryl, amino, nitro, loweralkylamino, diloweralkylamino, cyano, COOH, COO loweralkyl, amido, loweralkylamido, diloweralkylamido, CHO, diloweralkoxymethyl, CH=NOH, CH=NO loweralkyl, CH=NOCO loweralkyl, hydroxymethyl, loweralkoxymethyl, and $CH_2O$ acyl;

$R_3$ is a member selected from the group consisting of hydrogen, loweralkyl, loweralkenyl, and haloloweralkenyl;

$R_4$ is a member selected from the group consisting of hydrogen, hydroxymethyl, diloweralkoxymethyl, loweralkyl, cyanoethyl, CHO, loweralkoxymethyl, $CH_2O$ acyl, COOH, COO loweralkyl, CH=NOH, CH=NO loweralkyl, CH=NOCO loweralkyl, $(CH_2)_2COOH$, $(CH_2)_2COO$ loweralkyl, amidomethyl, aminoloweralkyl, loweralkylamino loweralkyl, diloweralkylamino loweralkyl, and

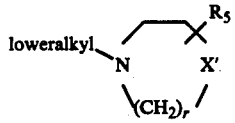

wherein

X' is a member selected from the group consisting of loweralkylamino, oxa, thia, and methylene; r is the integer 1, 2, or 3; and $R_5$ is a member selected from the group consisting of hydrogen, loweralkyl, hydroxyloweralkyl, loweralkanoyloxyloweralkyl, amino, and loweralkylamino.

X and Y are each members selected from the group consisting of hydrogen, halo, nitro, loweralkyl, loweralkoxy, aryl, hydroxy, acyloxy, aroyloxy, amino, loweralkylamino, diloweralkylamino, amido, loweralkylamido, diloweralkylamido, cyano, COOH, COO loweralkyl, CHO, $CH_2OH$, $CH_2O$ acyl, and $CH_2O$ aryl;

A considered separately is hydrogen;

B considered separately is a member selected from the group consisting of hydrogen, halo, loweralkyl, aryl, diloweralkylamino, COOH, COO loweralkyl, amido, loweralkylamido, diloweralkylamido, hydroxymethyl, $CH_2O$ acyl, and $CH_2O$ loweralkyl; and A and B considered together is a member selected from the group consisting of oxygen and sulfur.

As used herein, the terms "loweralkyl" and "loweralkoxy" mean straight or branched chain aliphatic hydrocarbons having from 1 to about 6 carbon atoms, such as for example methyl, ethyl, isopropyl, pentyl, and the like loweralkyls, and, respectively, methoxy, ethoxy, isopropoxy, pentoxy, and the like loweralkoxys. The term "halo" includes fluoro, chloro, bromo, and iodo. The terms "loweralkenyl" and "loweralkynyl" mean unsaturated, aliphatic hydrocarbons having from 2 to about 6 carbon atoms, such as for example ethenyl, 1-propenyl, 2-methyl-1-propenyl, 2-pentenyl, and the like loweralkenyls, and respectively, ethynyl, 1-propynyl, and 2-pentynyl, and the like loweralkynyls. The term "aryl" includes aromatic hydrocarbons such as naphthyl, phenyl and the like and substituted aromatic hydrocarbons such as phenyl substituted with from one to three members each selected from the group consisting of loweralkyl, loweralkoxy, halo and methylenedioxy, provided that only one such member is methylenedioxy (called herein "substituted phenyl"); and the like. The term "acyl" includes loweralkanoyl and aroyl radicals derived from carboxylic acids having the formula HCOOH, loweralkyl-COOH, and aryl-COOH. Examples of the acyl groups included herein are acetyl, propionyl, n-butyryl, and the like loweralkanoyls and benzoyl, naphthoyl, 3,5-dichlorobenzoyl, and the like aroyls.

The compounds of formulas (I) and (II) wherein $R_4$ is hydrogen and $R_1$, $R_2$, $R_3$, A, B, X, and Y are as originally defined may be prepared by reacting a substituted quinazoline of formula (III) or formula (IV) respectively, with a halo compound of formula (V), wherein Z is chloro or bromo, in a suitable cyclization solvent, such as an anhydrous loweralkanol (e.g. methanol, ethanol, isopropanol, and the like), a ketone (e.g. acetone), an aromatic hydrocarbon (e.g., benzene, toluene, xylene, and the like), an ether (e.g., diethyl ether), a cyclic ether (e.g. tetrahydrofuran, dioxane, and the like), an alkyl nitrile (e.g., acetonitrile), and the like, and mixtures thereof. The reaction may be conducted at temperatures down to about 0° C., but the reaction mixture is preferably heated, more preferably to the reflux temperature of the solvent. An intermediate quaternary halide salt product may be isolated by conventional methods, as for example by cooling and filtering the reaction mixture to separate the solid intermediate. To obtain the desired product, the halide salt is dissolved in water and the resulting solution treated with a weak base, such as for example sodium bicarbonate, sodium carbonate, potassium bicarbonate, and the like, or a dilute solution of a strong base such as an alkali metal hydroxide such as for example sodium or potassium hydroxide until hydrogen evolution ceases. It should be understood, however, that the intermediate quaternary salt need not be isolated. The desired product may be isolated from the aqueous mixture by conventional techniques, such as for example by extraction with a suitable organic solvent, such as for example an aromatic hydrocarbon as previously defined, an aliphatic halocarbon (e.g. carbon tetrachloride, chloroform, dichloromethane, and the like), ethyl acetate, and the like, followed by drying of the extract and removal of the organic solvent. This reaction scheme may be illustrated by the following:

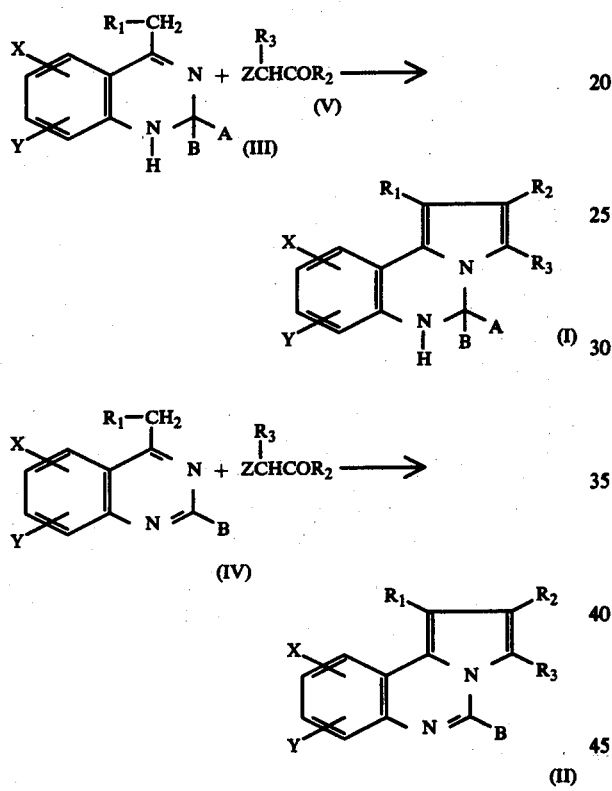

This method is preferred for those compounds of formula (I) and (II) wherein $R_1$ is a member selected from the group consisting of COO loweralkyl, CN, COOH, $CH_2OH$, CH(O loweralkyl)$_2$, nitro and loweralkyl; $R_2$ is a member selected from the group consisting of loweralkyl, COO loweralkyl, phenyl, substituted phenyl, and loweralkenyl; $R_4$ is hydrogen; and $R_3$, A, B, X, and Y are as originally defined.

The compounds of formula (I) wherein A and $R_4$ are hydrogen and $R_1$, $R_2$, $R_3$, B, X, and Y are as originally defined may also be obtained by hydrogenation of the above compounds of formula (II) by techniques well-known in the art, such as for example by subjecting them to hydrogen under atmospheric or elevated pressure in the presence of a suitable noble metal catalyst such as platinum oxide, palladium, or the like. This reaction scheme may be illustrated by the following:

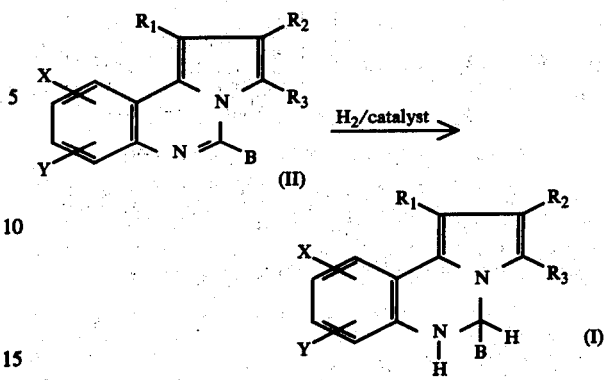

The compounds of formula (I) wherein A and B are taken together, $R_1$, X, and Y are as originally defined, $R_2$, and $R_3$ are each a member selected from the group consisting of hydrogen and loweralkyl, provided that one of said $R_2$ and $R_3$ is loweralkyl, and $R_4$ is hydrogen may be prepared by reacting a substituted quinazoline of formula (III) with an excess of a substituted chloroketone of formula (VI) in a suitable cyclization solvent as previously defined. The reaction mixture is preferably heated, more preferably to the reflux temperature of the solvent. The desired product may be obtained from the reaction mixture by conventional methods, as for example by chromatography followed by recrystallization. This reaction scheme may be illustrated by the following:

The compounds of formulas (I) and (II) prepared above may then be modified by chemical reactions of well-known types to alter certain substituent groups. It is well understood in the chemical art that certain groups may be altered or certain groups substituted while leaving the remainder of the molecule undisturbed, as shown in such well-known texts as "Organic Chemistry" by Morrison and Boyd, Allyn and Bacon (1959). Thus, an ester may be reduced to an alcohol or converted to an amide; an acetal may be hydrolyzed to an aldehyde, then converted to an oxime by treatment with hydroxylamine hydrochloride; an oxime may be converted into the corresponding oxime ethers or esters by reaction with an alkyl halide or an acyl halide or anhydride; an alcohol may be converted to an ether or ester by reaction with an alkyl halide or an acyl halide or anhydride; an aldehyde may be converted into an acetal by reaction with an alcohol; a nitro compound may be reduced to an amine; a carboxylic acid may be converted to an amine by the Schmidt reaction; N-unsubstituted compounds may be substituted with a host of groups, as discussed below and illustrated in Table I; and the like.

The compounds of formula (I) wherein A, B, X, Y and $R_3$ are as originally defined, $R_4$ is hydrogen, and $R_1$ and $R_2$ are both hydroxymethyl may be prepared by reduction of the corresponding compound of formula (I) wherein $R_1$ and $R_2$ are both COO loweralkyl by procedures well-known in the art. Suitable reducing agents are, for example, lithium aluminum hydride, diborane, and the like, and suitable solvents are ethers such as diethyl ether and tetrahydrofuran. As this reduction is generally exothermic, heating is not preferred. This reaction may be illustrated by the following:

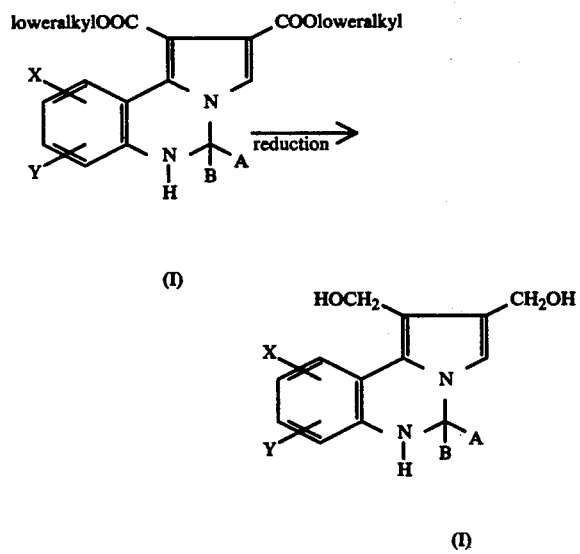

Likewise, the corresponding compound of formula (I) wherein $R_1$ and $R_2$ are both amido or substituted amido may be prepared by treatment of the same starting compound ($R_1=R_2=$COO loweralkyl) with aqueous or liquid ammonia, or the suitable amine, respectively. This reaction may be illustrated by the following:

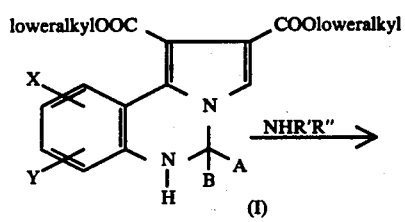

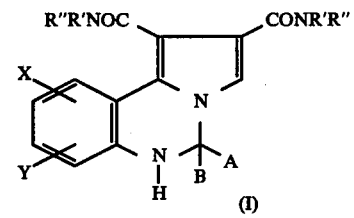

where R' and R'' are each members selected from the group consisting of hydrogen and loweralkyl.

The compounds of formula (I) wherein A, B, X, Y, and $R_3$ are as originally defined, $R_4$ is hydrogen, and $R_1$ or $R_2$ or both are members selected from the group consisting of CH=NOH, CH=NO acyl, and CH=NO loweralkyl may be prepared from the corresponding compounds of formula (I) wherein $R_1$ or $R_2$ or both are CH(O loweralkyl)$_2$ as follows. Whichever of $R_1$ and $R_2$ is not selected from the above group is as originally defined. The acetal ($R_1$=CH(O loweralkyl)$_2$) is hydrolyzed to the corresponding aldehyde by selective hydrolysis using a suitable acid such as for example acetic acid (preferably 80% aqueous acetic acid), p-toluenesulfonic acid in acetone, or the like. These acids will hydrolyze the acetal without hyrolyzing any other substituent groups (e.g. ester). Treatment of the aldehyde with hydroxylamine hydrochloride in a suitable solvent such as pyridine or dimethyl sulfoxide (DMSO) yields the corresponding oxime ($R_1$=CH=NOH). From the oxime may be prepared the corresponding oxime esters ($R_1$=CH=NOacyl) and ethers ($R_1$=CH=NOloweralkyl) by reaction with an acyl halide or anhydride, or a loweralkyl halide, respectively. Aprotic solvents such as aromatic hydrocarbons (e.g., benzene, toluene, xylene), halocarbons (e.g., chloroform, carbon tetrachloride, dichloromethane), pyridine, and the like are suitable solvents. This reaction scheme may be illustrated by the following for $R_1$:

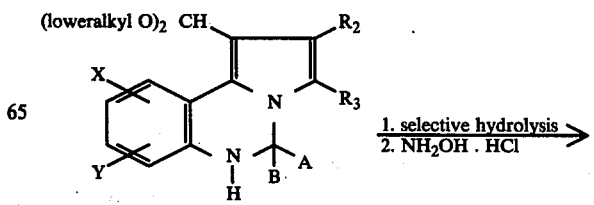

-continued

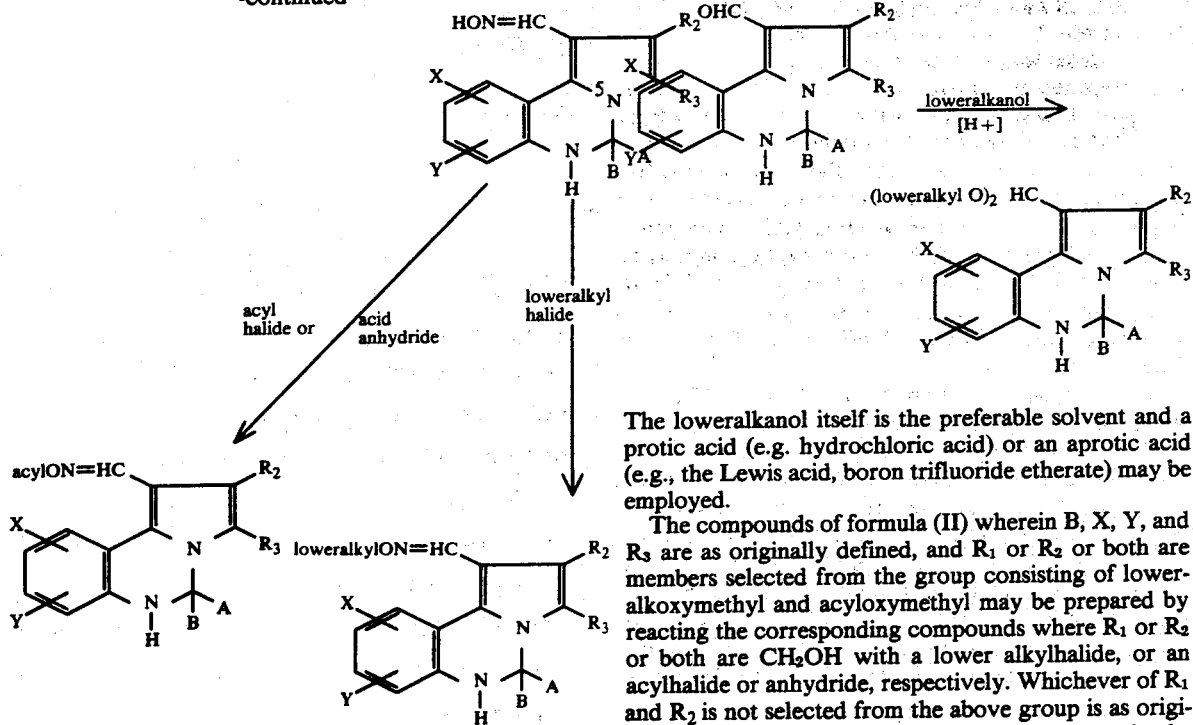

The compounds of formula (I) wherein A, B, X, Y, and $R_3$ are as originally defined, $R_4$ is hydrogen, and $R_1$ or $R_2$ or both are CH(O loweralkyl)$_2$ may also be prepared by reacting the corresponding loweralkanol in the presence of acid with a corresponding compound of formula (I) wherein $R_1$ or $R_2$ or both are CHO. Whichever of $R_1$ and $R_2$ is not CH(O loweralkyl)$_2$ is as originally defined. This reaction, which is the reverse of the selective hydrolysis above, may be illustrated by the following for $R_1$:

The loweralkanol itself is the preferable solvent and a protic acid (e.g. hydrochloric acid) or an aprotic acid (e.g., the Lewis acid, boron trifluoride etherate) may be employed.

The compounds of formula (II) wherein B, X, Y, and $R_3$ are as originally defined, and $R_1$ or $R_2$ or both are members selected from the group consisting of loweralkoxymethyl and acyloxymethyl may be prepared by reacting the corresponding compounds where $R_1$ or $R_2$ or both are CH$_2$OH with a lower alkylhalide, or an acylhalide or anhydride, respectively. Whichever of $R_1$ and $R_2$ is not selected from the above group is as originally defined. This reaction may be conducted in the same manner as the above-described reaction with the oximes of formula (I). The corresponding loweralkoxymethyl compounds of formula (I) may be prepared by hydrogenation of the loweralkoxymethyl compounds of formula (II), using the same conditions previously described for the hydrogenation of compounds of formula (II). These reactions may be illustrated by the following for $R_1$:

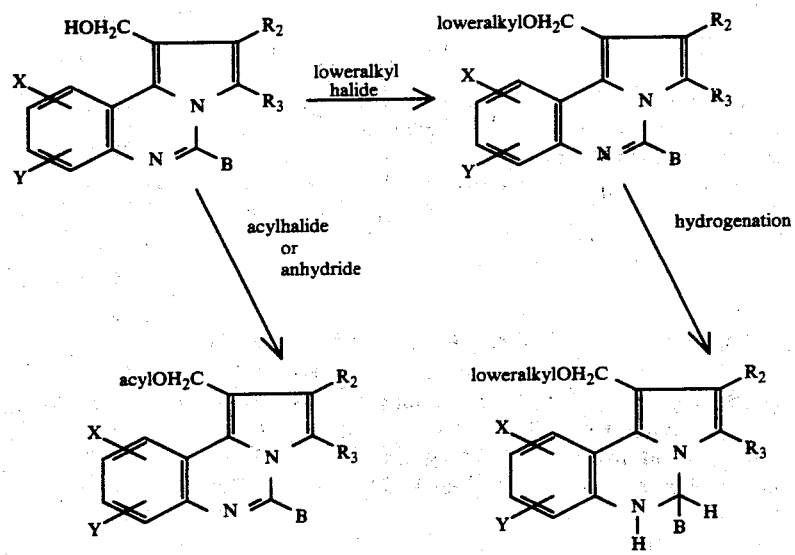

The compounds of formula (I) wherein B, X, Y, and $R_3$ are as originally defined, A and $R_4$ are hydrogen, and $R_1$ or $R_2$ or both are amino may be prepared by reduction of the corresponding compounds of formula (II) wherein $R_1$ or $R_2$ or both are nitro. Whichever of $R_1$ and $R_2$ is not amino is as originally defined. This reduction may be catalytic (e.g. H$_2$/PtO$_2$) or non-catalytic (e.g. LiAlH₄) and is conducted as previously described for each type. This reaction may be illustrated by the following for R₁:

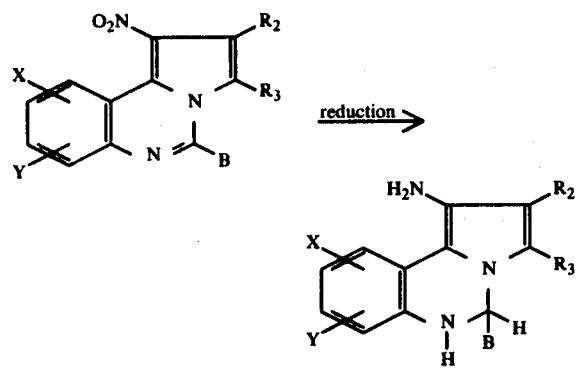

The compounds of formula (II) wherein R₃, B, X, and Y are as originally defined and either R₁ or R₂ or both are amino may be prepared by reacting the corresponding compounds wherein either R₁ or R₂ or both are COOH with hydrazoic acid in the presence of sulfuric acid by the well-known Schmidt reaction. Whichever of R₁ and R₂ is not amino is as originally defined. This reaction may be illustrated by the following for R₂:

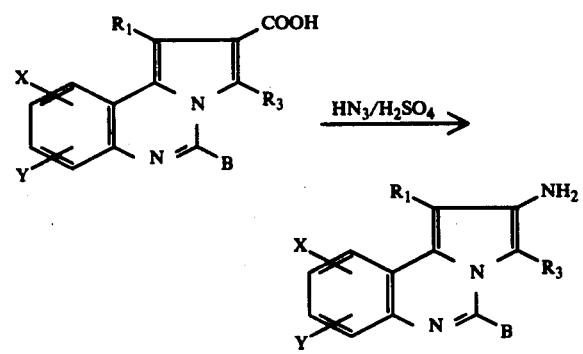

Substitution of the 6-nitrogen on the compounds of formula (I) may be effected by reaction of the corresponding unsubstituted compound with a nitrogen-substituting reagent. Such reagents and the procedure for effecting substitution are well known in the chemical art. Typical nitrogen-substituting reagents are formic acid, ClCOO loweralkyl, halo-substituted loweralkenes, and the like, wherein n, r, X', and R₅ are as originally defined. The resulting N-substituted compounds may then be reduced, hydrolyzed, aminated, or the like to effect changes in the N-substituting group. In this way compounds of formula (I) having R₄ groups as originally described may be prepared. These reactions may be illustrated by the following:

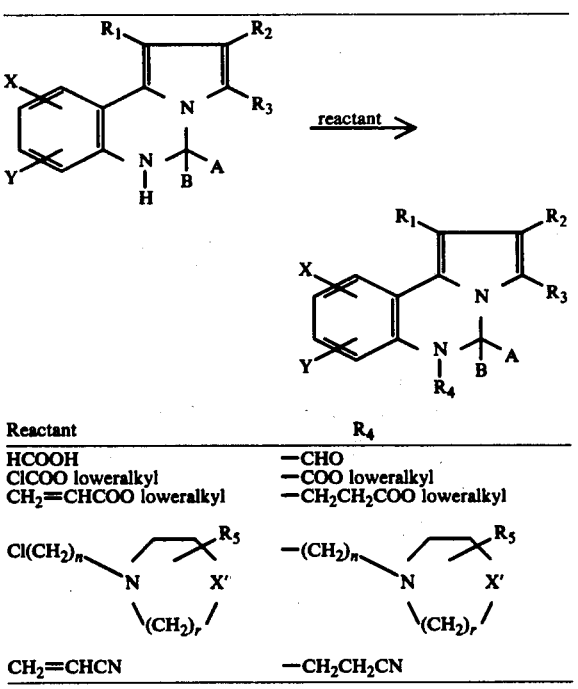

| Reactant | R₄ |
|---|---|
| HCOOH | —CHO |
| ClCOO loweralkyl | —COO loweralkyl |
| CH₂=CHCOO loweralkyl | —CH₂CH₂COO loweralkyl |
| Cl(CH₂)ₙ−N(−(CH₂)ᵣ−)−R₅ X″ | —(CH₂)ₙ−N(−(CH₂)ᵣ−)−R₅ X' |
| CH₂=CHCN | —CH₂CH₂CN |

The resulting N-substituted compounds of formula (I) may be reacted as described above for the N-unsubstituted compounds to modify the nature of the substituting group. The following Table I illustrates the possible modifications, where R' and R" are as previously defined.

TABLE I

| Original R₄ | Reagent/Reaction | Resulting R₄ |
|---|---|---|
| —CHO | reduction (diborane) | —CH₃ |
| —CHO | (loweralkyl)₃O⁺BF₄⁻ | —CH(O loweralkyl)₂ |
| —CH(O loweralkyl)₂ | hydrolysis, NH₂OH . HCl | —CH=NOH |
| —CH=NOH | loweralkyl halide | —CH=NO loweralkyl |
| —CH=NOH | acyl halide | —CH=NO acyl |
| —COO loweralkyl | reduction (LiAlH₄ or diborane) | —CH₂OH* |
| —CH₂OH | loweralkyl halide | —CH₂O loweralkyl |
| —CH₂OH | acyl halide | —CH₂O acyl |
| —CH₂OH | Cl(CH₂)₂N-(loweralkyl)₂ | —CH₂O(CH₂)N(loweralkyl)₂ |
| —COO loweralkyl | hydrolysis | —COOH |
| —COO loweralkyl | NHR'R" | —CONR'R" |
| —CH₂CH₂COO loweralkyl | reduction (LiAlH₄ or diborane) | —CH₂CH₂CH₂OH* |
| —CH₂CH₂COO loweralkyl | hydrolysis | —CH₂CH₂COOH |
| —CH₂CH₂COO loweralkyl | NHR'R" | —CH₂CH₂CONR'R" |
| —CH₂CH₂CN | reduction (LiAlH₄ or diborane) | —CH₂CH₂CH₂NH₂* |

These reactions may occur in concert with the identical modification of another R-group as described above or may occur individually.
* A=B=H The compounds of the invention possess cardiovascular activities and are useful in the treatment of hypertension and bradycardia and as cardiotonic agents, as shown by their activity in the spontaneous hypertensive rat test at dosages from about 50 mg/kg to about 100 mg/kg body weight. They have also been found to inhibit cyclic AMP phosphodiesterase at dosages from about 10 to about 900 mg/kg/day, thereby providing an increase in the intracellular concentration of adenosine-3',5'-cyclic monophosphate, and are therefore useful as antiasthmatic agents. A preferred dosage range is from about 200 to about 250 mg/kg/day. The compounds of the invention are also useful for treatment of cardiac arrythmia as shown by their activity in eliminating chloroform-induced arrythmia in the mouse at dosages from about 30 to about 150 mg/kg.

In view of the activities of the subject compounds there are provided herein methods for treating a patient or subject having an ailment selected from hypertension, bradycardia, and cardiac arrythmia which comprises systemically administering to said patient or subject an effective amount of said compounds for treatment of said ailment, in base or acid addition salt form, preferably in admixture with a pharmaceutically-acceptable carrier. The methods of the invention are seen to be particularly suitable for use in treating warm-blooded animals.

To prepare the pharmaceutical compositions of this invention, a compound of formulas (I) or (II) or salt thereof is combined as the active ingredient in intimate admixture with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions herein will generally contain, per dosage unit, e.g., tablet, capsule, powder, injection, teaspoonful and the like, from about 5 to about 500 mg and preferably from about 10 to about 250 mg.

Certain preferred compounds of the invention are those of formula (I) wherein X is a member selected from the group consisting of halo, hydrogen, and loweralkoxy; Y is hydrogen; $R_1$ is a member selected from the group consisting of hydrogen and COO loweralkyl; $R_2$ is a member selected from the group consisting of hydrogen, loweralkyl, hydroxymethyl, and COO loweralkyl; $R_3$ is a member selected from the group consisting of hydrogen, halo, loweralkyl, loweralkenyl, and halo-substituted loweralkenyl; $R_4$ is a member selected from the group consisting of hydrogen, loweralkyl, hydroxy-loweralkyl, cyanoethyl, CHO, COO loweralkyl, $CH_2CH_2COO$ loweralkyl, and $CH_2CH_2COOH$; and A and B are selected from the group consisting of both hydrogen, and hydrogen and loweralkyl (considered separately), and oxygen (considered together).

Other preferred compounds of the invention are those of formula (II) wherein $R_1=R_3=Y=$hydrogen; X is a member selected from the group consisting of hydrogen, halo, loweralkoxy, and cyano; B is a member selected from the group consisting of hydrogen and loweralkyl; and $R_2$ is a member selected from the group consisting of COOH and COO loweralkyl.

The subject compounds may be isolated as the free base or in the form of an acid addition salt by the synthetic process normally employed. These compounds, in base form, are convertible to therapeutically active acid addition salts by treatment with an appropriate acid, such as, for example, an inorganic acid, such as, a hydrohalic acid, e.g., hydrochloric, hydrobromic, hydroiodic acid; sulfuric or nitric acid; a phosphoric acid; an organic acid, such as, acetic, propionic, glycolic, lactic, pyruvic, malonic, succinic, maleic, fumaric, malic, tartaric, citric, benzoic, cinnamic, mandelic, methanesulfonic, p-toluenesulfonic, cyclohexanesulfamic, salicyclic, p-aminosalicyclic, 2-phenoxybenzoic, or 2-acetoxybenzoic acid. Conversely, the salt form can be converted in the usual manner into the free base.

The substituted quinazolines from which the compounds of the invention are made are generally known or can be prepared by known procedures, as taught in the following articles and book: Schoefield, *J. Chem. Soc.*, 1927(1952); Albert, *J. Chem. Soc.*, 505(1954); Armarego, *J. Chem. Soc.*, (C) 234 (1966); and "Part I-Quinazolines" by W. L. F. Armarego in "Fused Pyrimidines," D. J. Brown, ed., Interscience, 1967. The halo compounds of formulas (V) and (VI) are also generally known or can be prepared by known procedures.

The present invention is illustrated by the following examples.

EXAMPLE I

2-Carbethoxy-1H-pyrrolo[1,2-c]quinazolin-4-ium bromide

A solution of ethyl bromopyruvate (32.76 g, 0.172 m) and 4-methylquinazoline (15.61g, 0.109 m) in dry ethanol (400 ml) was heated at reflux for 16 hours during which time a yellow precipitate formed. The reaction mixture was cooled and the solid filtered and dried to yield crude product. Crystallization from MeOH afforded the product as a yellow solid; m.p. 274°-275° C.

Anal: Calcd for $C_{14}H_{13}BrN_2O_2$: C, 52.33; H, 4.05; N, 8.72. Found: C, 52.30; H, 4.06; N, 8.75.

EXAMPLE II

2-Carbethoxypyrrolo[1,2-c]quinazoline:

A solution of ethyl bromopyruvate (3.2g, 0.016 m) and 4-methylquinazoline (2.0g, 0.014 m) in dry ethanol (150 ml) was heated at reflux for two hours. During this time, a tan solid formed. Excess ethyl bromopyruvate was added (1.0g) and the reaction mixture was allowed to reflux overnight. After this time, the reaction was complete. The alcohol was removed in vacuo and the residue diluted with $H_2O$. Sodium bicarbonate was added until effervescence ceased and the aqueous mixture extracted with ether. The ether extracts were combined, dried over $Na_2SO_4$, filtered and the solvent removed in vacuo to yield a tan solid. Crystallization from MeOH afforded the product as a white solid; m.p. 138°-139° C.

Anal. Calcd for $C_{14}H_{12}N_2O_2$: C, 69.99; H, 5.03; N, 11.66. Found: C, 70.11; H, 5.17; N, 11.66.

EXAMPLE III

2-Hydroxymethyl-5,6-dihydropyrrolo[1,2-c]quinazoline

LiAlH$_4$ (0.50 g, 0.013 m) was slurried in ether (200 ml) and to this was added a solution of the product of Example II (1.0 g, 0.007 m) in ether (50 ml). The reaction mixture was stirred at room temperature for 2 hrs. Water (30 ml) was added and the mixture was acidified with 10% HCl. The resulting mixture was extracted with ether, the ether extracts combined, dried over Na$_2$SO$_4$, filtered, and the solvent removed in vacuo to yield 1.02 g of a white solid. Crystallization from EtOAc/hexane afforded the product as a white solid; m.p. 128°-130° C.

Anal. Calcd for $C_{12}H_{12}N_2O$: C, 71.98; H, 6.04; N, 13.99. Found: C, 71.63; H, 6.09; N, 14.02.

EXAMPLE IV

2-Carbethoxy-5,6-dihydropyrrolo[1,2-c]quinazoline

The product of Example II (2.5 g, 0.01 m) was dissolved in MeOH (250 ml). The catalyst, PtO$_2$ (0.5 g), was added and the mixture was hydrogenated at 42 p.s.i. for 3 hrs. Filtration and removal of the solvent in vacuo yielded a white solid. Crystallization from MeOH afforded the product as a white solid; m.p. 140°-141° C.

Anal; Calcd for $C_{14}H_{14}N_2O_2$: C, 69.14; H, 5.82; N, 11.56. Found: C, 69.80; H, 5.99; N, 11.90.

EXAMPLE V

Pyrrolo-[1,2-c]quinazoline-2-carboxylic acid hemihydrate

A solution of the product of Example II (2.0 g, 0.008 m) and KOH (2.0 g, 0.036 m) in MeOH (20 ml) and H$_2$O (20 ml) was refluxed for 1 hr. The methanol was removed under vacuum and the resulting aqueous solution was acidified with HCl (10% aqueous). When the solution became acidic, a white solid formed. It was filtered and washed well with H$_2$O and dried, to yield 1.23 g of crude product. Crystallization from MeOH afforded the product as an off-white solid; m.p. 323°-325° C.

Anal. Calcd for $C_{12}H_8N_2O_2 \cdot \frac{1}{2}H_2O$: C, 65.14; H, 4.07; N, 12.65. Found: C, 65.54; H, 3.82; N, 12.54.

EXAMPLE VI

2-Carbethoxy-5,6-dihydropyrrolo[1,2-c]quinazoline-6-propionic acid ethyl ester hydrochloride To a suspension of the product of Example IV (0.8 g, 0.0033m) in ethyl acrylate (5 ml), cooled to 0°-5°, was added, dropwise, 0.1 ml of Triton B (benzyltrimethylammonium hydroxide) over 3 min. An exothermic reaction resulted and a brown colored solution formed. The reaction mixture was refluxed for 72 hours. The excess of ethyl acrylate was distilled in vacuo to yield a dark brown semi-solid residue (1.0 g). The residue was dissolved in CHCl$_3$ and chromatographed on a 50 g Silicar column prepared in CHCl$_3$. The column was eluted with CHCl$_3$ to afford 0.75 g of an oily product. A solution of this oily product in ether (50 ml) was treated with excess HCl (g). A white solid formed immediately and was filtered, washed with ether, and air dried. Rapid crystallization from cold CHCl$_3$/hexane afforded the desired product; m.p. 90°-94° C.

Anal. Calcd. for $C_{19}H_{22}N_2O_4 \cdot HCl$: C, 60.24; H, 6.12; N, 7.39. Found: C, 60.43; H, 5.98; N, 7.62.

EXAMPLE VII

2-Carbethoxy-5,6-dihydropyrrolo[1,2-c]quinazoline-6-propionitrile

To a suspension of the product of Example IV (1.5 g, 0.0062 m) in acrylonitrile (5 ml), cooled to 0°-5°, was added, dropwise, 0.4 ml of Triton B over 3 min. An exothermic reaction resulted and a brown colored solution formed. After 5 hr. of reflux, the excess of acrylonitrile was distilled in vacuo, and the semi-solid residue (0.95 g) was crystallized from methanol to afford the desired product; m.p. 102°-104° C.

Anal. Calcd for $C_{17}H_{17}N_3O_2$: C, 69.13; H, 5.80; N, 14.23. Found: C, 68.81; H, 5.91; N, 14.21.

EXAMPLE VIII

2-Carboxy-5,6-dihydropyrrolo[1,2-c]quinazoline-6-propionic acid

A solution of the product of Example VI (2.75 g, 0.008 m) and KOH (4.0 g, 0.072 m) in MeOH (40 ml) and H$_2$O (40 ml) was refluxed for 4 hr. The methanol was removed under vacuum and the resulting aqueous solution was acidified with HCl (10% aqueous). When the solution became acidic, a greenish solid formed. It was filtered and washed with H$_2$O and dried, to yield 2.2 g of crude product. Crystallization from MeOH afforded the desired product; m.p. 234°-236°.

Anal: Calcd for $C_{15}H_{14}N_2O_4$: C, 62.93; H, 4.93; N, 9.79. Found: C, 63.22; H, 5.21; N, 9.87.

EXAMPLE IX 2,6-Dicarbethoxy-5,6-dihydropyrrolo[1,2-c]quinazoline

A solution of the product of Example IV (1.2 g, 0.005 m) and ethyl chloroformate (6.0 g, 0.0553 m) in acetone (20 ml) and H$_2$O (50 ml) was treated with NaOH (0.1 ml aq. 30%) and the mixture stirred at room temperature for 15 min. The acetone was removed in vacuo and the aqueous residue cooled in an ice-bath. A solid formed and this was filtered, washed with water, and dried in vacuo. The crude product (1.0 g) was crystallized from methanol to afford the desired product; m.p. 80°-82° C.

Anal. Calcd for $C_{17}H_{18}N_2O_4$: C, 64.95; H, 5.77; N, 8.91. Found: C, 64.68; H, 5.79; N, 8.88.

EXAMPLE X

2-Carbethoxy-5,6-dihydropyrrolo-6-formyl-[1,2-c]quinazoline

The product of Example IV (2.1 g, 0.0086 m) was refluxed for 10 min with dry formic acid (20 g, 0.436 m) and then cooled in an ice-bath. Water (300 ml) was added and the white solid (2.15 g) filtered. The crude solid was crystallized from acetone to afford the desired product; m.p. 131°-133°.

Anal. Calcd for $C_{15}H_{14}N_2O_3$: C, 66.66; H, 5.22; N, 10.36. Found: C, 66.59; H, 5.14; N, 10.42.

EXAMPLE XI

2-Carbethoxy-5,6-dihydropyrrolo-6-methyl[1,2-c]quinazoline

Diborane (60 ml of a 0.96 M solution in THF) was added through a serum stopper to a mixture of the product of Example X (3.0 g, 0.010 m) in dry THF (150 ml).

The solution was allowed to stir under nitrogen at room temperature for 30 min, and excess diborane was carefully destroyed with MeOH (10 ml). The solvents were removed in vacuo to afford a yellow solid (2.4 g). Crystallization from MeOH yielded the desired product as a white solid; m.p. 82°–84°.

Anal. Calcd for $C_{15}H_{16}N_2O_2$: C, 70.29; H, 6.29; N, 10.93. Found: C, 70.13; H, 6.20; N, 10.95.

EXAMPLE XII

2-Hydroxymethyl-6-methyl-5,6-dihydropyrrolo[1,2-c]quinazoline

LiAlH$_4$ (16.75 g, 0.442 m) was slurried in ether (1000 ml) and to this was added a solution of the product of Example XI (27.92 g, 0.109 m) in ether (500 ml). The reaction mixture was stirred at ambient temperature for 1½ hr. To the reaction mixture was added dropwise and successively H$_2$O (17.0 ml), NaOH (17.0 ml of 15% aqueous) and H$_2$O (51 ml). The precipitate was filtered and washed with ether. The solvent was removed in vacuo to yield the desired product as a white solid; m.p. 74°–76° C.

Anal. Calcd for $C_{13}H_{14}N_2O$: C, 72.87; H, 6.59; N, 13.07. Found: C, 72.91; H, 6.66; N, 12.83.

EXAMPLE XIII 1,2-Dicarbethoxypyrrolo[1,2-c]quinazoline

A solution of ethyl bromopyruvate (8.0 g, 0.1041 m) and ethyl 4-quinazolylacetate prepared according to the procedure of Elderfield and Serlin, *J. Org. Chem.* 16, 1669 (1951) (2.32 g, 0.011 m) in dry EtOH (250 ml) was heated at reflux for 24 hr. Sodium bicarbonate was added until effervescence ceased. A solid formed and this was filtered, washed well with H$_2$O, and dried. The crude product (1.8 g) was chromatographed on 150 g of Silicar. The desired product was eluted with 3% EtOAc/benzene. Crystallization from MeOH afforded the desired product as a white solid; m.p. 125°–126° C.

Anal. Calcd for $C_{17}H_{16}N_2O_4$: C, 65.38; H, 5.16; N, 8.97. Found: C, 65.56; H, 5.15; N, 8.96.

EXAMPLE XIV

2-Carbethoxy pyrrolo[1,2-c]quinazolin-6[H]-5-one

A solution of ethylbromopyruvate (29.25 g, 0.15 m) and 4-methyl-2-hydroxy quinazoline (12.00 g, 0.075 m) in dry ethanol (500 ml) was heated at reflux for 24 hours. During this time a tan solid formed. The reaction mixture was concentrated in vacuo to ⅓ volume, cooled, and the tan solid filtered. The filtrate was evaporated in vacuo to yield a dark brown gum (8.52 g). The resulting tan solid was slurried in H$_2$O (300 ml) and sodium bicarbonate was added until effervescence ceased. The aqueous solution was extracted with ether. The ether extracts were combined, dried over Na$_2$SO$_4$, filtered, and the solvent removed to yield a yellow solid. Crystallization from MeOH afforded the desired product as a pale yellow solid; m.p. 239°–241° C.

Anal. Calcd for $C_{14}H_{12}N_2O_3$: C, 65.62; H, 4.72; N, 10.93. Found: C, 65.61; H, 4.73; N, 11.13.

EXAMPLE XV

2-Carbethoxy-6-(β-carbethoxyethyl)pyrrolo[1,2-c]quinazolin-6[H]5-one

Triton B (0.3 ml) was added dropwise over a 3 minute period to a cooled suspension (0°–5°) of the product of Example XIV (2.2 g, 0.0085m) in ethyl acrylate (15 ml). An exothermic reaction resulted and a brown colored solution formed. The excess of ethyl acrylate was distilled in vacuo to yield a dark brown semi-solid residue (2.9 g). The residue was dissolved in CHCl$_3$ and chromatographed on a 150 g Silicar column prepared in CHCl$_3$. The column was eluted was CHCl$_3$ to afford an oily product (2.1 g, 70%), which after crystallization from MeOH afforded the desired product; m.p. 104°–106° C.

Anal. Calcd for $C_{19}H_{20}N_2O_5$: C, 64.04; H, 5.66; N, 7.86. Found: C, 64.24; H, 5.53; N, 7.98.

EXAMPLE XVI

2-Carbethoxy-6-(β-cyanoethyl)pyrrolo[1,2-c]quinazolin-6[H]-5-one

Triton B (1 ml) was added dropwise over a 5 min period to a cooled (0°–5°) suspension of the product of Example XIV (2.1 g, 0.0081 m) in acrylonitrile (20 ml). An exothermic reaction resulted and a brown colored solution formed. After 3 hr. of reflux, the excess of acrylonitrile was distilled in vacuo, and the solid residue was crystallized from acetonitrile to afford the desired product; m.p. 191°–193° C.

Anal. Calcd for $C_{17}H_{15}N_3O_3$: C, 66.01; H, 4.89; N, 13.59. Found: C, 66.06; H, 5.13; N, 13.49.

EXAMPLE XVII

2-Methylpyrrolo[1,2-c]quinazolin-6[H]-5-one

A solution of chloroacetone (58.8 g, 0.66 m) and 4-methyl-2-hydroxyquinazoline (12.0 g, 0.066m) in dry ethanol (1500 ml) was heated at reflux for 68 hr. The reaction mixture was concentrated to dryness in vacuo to yield a dark brown semisolid. This was slurried in H$_2$O and treated with excess NaHCO$_3$. The aqueous mixture was extracted with ether (4 × 200 ml) and CHCl$_3$ (4 × 200 ml). The organic extracts were combined, dried over Na$_2$SO$_4$, filtered, and the solvent removed in vacuo to yield 24.43 g of a dark brown semisolid. The semisolid was chromatographed on a 1000 g Silicar column prepared in benzene and eluted with benzene to give the desired product. Crystallization from MeOH yielded the pure product as a white solid, m.p. 244°–245° C.

Anal. Calcd for $C_{12}H_{10}N_2O$: C, 72.71; H, 5.08; N, 14.13. Found: C, 72.44; H, 5.07; N, 14.15.

EXAMPLE XVIII 3-(2-Chloro-1-propenyl)-2-methylpyrrolo[1,2-c]guinazoline-6[H]-5-one A solution of chloroacetone (106.84 g, 1.18 m) and 4-methyl-2-hydroxyquinazoline (24.0 g, 0.132 m) in dry EtOH (3000 ml) was heated at reflux for 68 hr. The reaction mixture was concentrated to dryness in vacuo to yield a dark brown semisolid. This was slurried in H$_2$O and treated with excess NaHCO$_3$. The aqueous mixture was extracted with ether (4 × 400 ml) and CHCl$_3$ (4 × 400 ml). The organic extracts were combined, dried over Na$_2$SO$_4$, filtered, and the solvent removed in vacuo to yield 34.5 g of a dark brown semisolid. The semisolid was chromatographed on a 2000 g Silicar column prepared in benzene. Elution with benzene yielded the desired product, crystallization of which from MeOH yielded a white solid; m.p. 205°–206° C.

Anal. Calcd for $C_{15}H_{13}ClN_2O$: C, 66.08; H, 4.77; N, 10.27. Found: C, 65.88; H, 4.79; N, 10.31.

EXAMPLE XIX

3-Methylpyrrolo[1,2-c]quinazolin-6[H]-5-one

A solution of chloroacetone (106.84 g, 1.18 ml) and 4-methyl-2-hydroxyquinazoline (24.0 g, 0.132 m) in dry EtOH (3000 ml) and was heated at reflux for 68 hr. The reaction mixture was concentrated to dryness in vacuo to yield a dark brown semisolid. This was slurried in H$_2$O and treated with excess NaHCO$_3$. The aqueous mixture was extracted with ether (4 × 400 ml) and CHCl$_3$ (4 × 400 ml). The organic extracts were combined, dried over Na$_2$SO$_4$, filtered, and the solvent removed in vacuo to yield 34.5 g of a dark brown semisolid. The semisolid was chromatographed on a 2000 g Silicar column prepared in benzene. Elution with benzene yielded the product of Example XVIII, followed by the desired product; m.p. 251°-252° C.

Anal. Calcd for C$_{12}$H$_{10}$N$_2$O: C, 72.71; H, 5.08; N, 14.13. Found: C, 72.35; H, 4.94; N, 13.83.

EXAMPLE XX

2-Methyl-6-(β-cyanoethyl)-pyrrolo[1,2-c]quinazolin-6[H]-5-one

Triton B (1 ml) was added dropwise over a 5 min period to a cooled (0°-5°) suspension of the product of Example XVII (2.8 g, 0.0141 m) in acetonitrile (100 ml) and acrylonitrile (30 ml). An exothermic reaction resulted and a brown colored solution formed. After 3 hr of reflux, the solvent and the excess of acrylonitrile were distilled in vacuo. The solid residue (3.5 g) was crystallized from ethanol to afford the desired product; m.p. 161°-163° C.

Anal. Calcd for C$_{15}$H$_{13}$N$_3$O: C, 71.70; H, 5.21; N, 16.72. Found: C, 72.03; H, 5.23; N, 16.82.

EXAMPLE XXI

Following the procedure of Example II, but substituting for the ethyl bromopyruvate and 4-methylquinazoline used therein equivalent amounts of the suitable reactants, the following respective compounds are prepared:

| X | Y | B | R$_1$ | R$_2$ | R$_3$ |
|---|---|---|---|---|---|
| H | 7-OH | H | H | COOC$_2$H$_5$ | H |
| H | 7-OCH$_3$ | H | H | " | H |
| H | H | Cl | H | " | H |
| H | H | OCH$_3$ | H | " | H |
| H | H | N(CH$_3$)$_2$ | H | " | H |
| 10-CH$_3$ | H | H | H | CH$_3$ | CH$_3$ |
| 10-CH$_3$ | H | CH$_3$ | H | CH$_3$ | CH$_3$ |
| 10-CH$_3$ | 7-CH$_3$ | CH$_3$ | H | COOCH$_3$ | H |
| H | 7-Cl | C$_2$H$_5$ | H | " | H |
| 10-NO$_2$ | H | CH$_2$C$_6$H$_5$ | H | " | H |
| H | 7-CH$_3$ | C$_6$H$_5$ | H | C$_6$H$_5$ | CH=CH$_2$ |
| 10-Cl | 7-Cl | C$_6$H$_5$ | CH$_3$ | COOCH$_3$ | CH=CH$_2$ |
| 10-C$_6$H$_5$ | H | CH$_3$ | H | " | H |
| 10-C$_2$H$_5$ | H | CF$_3$ | H | " | H |
| 10-OC(O)—CH$_3$ | H | i-C$_3$H$_7$ | H | " | H |
| H | 7-C$_6$H$_5$COO | H | C$_6$H$_5$ | " | H |
| H | 7-NH$_2$ | H | CH$_3$ | " | H |
| 10-CH$_2$CONH$_2$ | H | H | NO$_2$ | COOC$_2$H$_5$ | H |
| 10-N(CH$_3$)$_2$ | H | H | C$_2$H$_5$ | COOC$_2$H$_5$ | H |
| H | 7-CONH$_2$ | H | COOC$_2$H$_5$ | C$_6$H$_5$ | H |
| H | 7-CONHCH$_3$ | H | CN | CH=CH$_2$ | H |
| H | 7-CON(CH$_3$)$_2$ | H | COOH | CH$_3$ | H |
| H | H | H | CH$_2$OH | COOC$_2$H$_5$ | H |
| H | H | H | CH(OC$_2$H$_5$)$_2$ | p-C$_6$H$_4$Cl | H |

EXAMPLE XXII

Following the procedure of Example IV, but substituting for the 2-carbethoxypyrrolo [1,2-c]quinazoline used therein, an equivalent amount of each of the products of Example XXI, the following respective compounds are prepared, wherein A is hydrogen:

| X | Y | B | R$_1$ | R$_2$ | R$_3$ |
|---|---|---|---|---|---|
| H | 7-OH | H | H | —COOC$_2$H$_5$ | H |
| H | 7-OCH$_3$ | H | H | " | H |
| H | H | Cl | H | " | H |
| H | H | OCH$_3$ | H | " | H |
| H | H | N(CH$_3$)$_2$ | H | " | H |

-continued

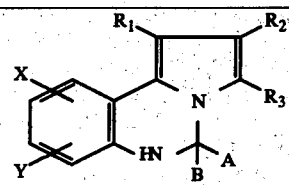

| X | Y | B | R₁ | R₂ | R₃ |
|---|---|---|---|---|---|
| 10-CH₃ | H | H | H | CH₃ | CH₃ |
| 10-CH₃ | H | CH₃ | H | CH₃ | CH₃ |
| 10-CH₃ | 7-CH₃ | CH₃ | H | —COOCH₃ | H |
| H | 7-Cl | C₂H₅ | H | " | H |
| 10-NH₂ | H | CH₂C₆H₅ | H | " | H |
| H | 7-CH₃ | C₆H₅ | H | C₆H₅ | C₂H₅ |
| 10-Cl | 7-Cl | C₆H₅ | CH₃ | —COOCH₃ | C₂H₅ |
| 10-C₆H₅ | H | CH₃ | H | " | H |
| 10-C₆H₅ | H | CF₃ | H | " | H |
| 10-OCCH₃ (O=) | H | i-C₃H₇ | H | " | H |
| H | 7-C₆H₅COO | H | C₆H₅ | " | H |
| H | 7-NH₂ | H | CH₃ | " | H |
| 10-CH₂CONH₂ | H | H | NH₂ | —COOCH₃ | H |
| 10-N(CH₃)₂ | H | H | C₂H₅ | —COOC₂H₅ | H |
| H | 7-CONH₂ | H | —COOC₂H₅ | C₆H₅ | H |
| H | 7-CONHCH₃ | H | —CH₂-NH₂ | C₂H₅ | H |
| H | 7-CON(CH₃)₂ | H | —COOH | CH₃ | H |
| H | H | H | CH₂OH | —COOC₂H₅ | H |
| H | H | H | CH(OC₂H₅)₂ | p-C₆H₄Cl | H |

EXAMPLE XXIII

Following the procedure of Example XIV, but substituting for the ethyl bromopyruvate and 4-methyl-2-hydroxyquinazoline equivalent amounts of the suitable reagents, the following respective products are obtained:

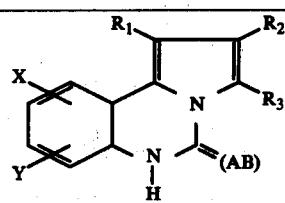

| X | Y | R₁ | R₂ | R₃ | AB |
|---|---|---|---|---|---|
| H | 7-OH | H | COOC₂H₅ | H | O |
| H | 7-OCH₃ | H | " | H | O |
| H | H | H | " | H | O |
| H | H | H | " | H | O |
| H | H | H | " | H | O |
| 10-CH₃ | H | H | CH₃ | CH₃ | O |
| 10-CH₃ | H | H | CH₃ | CH₃ | O |
| 10-CH₃ | 7-CH₃ | H | COOCH₃ | H | O |
| H | 7-Cl | H | " | H | O |
| 10-NO₂ | H | H | " | H | O |
| H | 7-CH₃ | H | C₆H₅ | CH=CH₂ | O |
| 10-Cl | 7-Cl | CH₃ | COOCH₃ | CH=CH₂ | O |
| 10-C₆H₅ | H | H | " | H | S |
| 10-C₆H₅ | H | H | " | H | S |
| 10-CH₃COO | H | H | " | H | S |
| H | 7-C₆H₅COO | C₆H₅ | " | H | S |
| H | 7-NH₂ | CH₃ | " | H | S |
| 10-CH₂CONH₂ | H | NO₂ | COOC₂H₅ | H | S |
| 10-N(CH₃)₂ | H | C₂H₅ | COOC₂H₅ | H | S |
| H | 7-CONH₂ | COOC₂H₅ | C₆H₅ | H | S |
| H | 7-CONHCH₃ | CN | CH=CH₂ | H | S |
| H | 7-CON(CH₃)₂ | COOH | CH₃ | H | S |
| H | H | CH₂OH | COOC₂H₅ | H | S |
| H | H | CH(OC₂H₅)₂ | p-C₆H₄Cl | H | S |

EXAMPLE XXIV

Following the procedure of Example VI, but substituting for the 2-carbethoxy-5,6-dihydropyrrolo[1,2-c]-quinazoline used therein an equivalent amount of each of the compounds produced in Examples XXII and XXIII, the corresponding compounds having the following general formula are produced, wherein X, Y, A, B, R₁, R₂, and R₃ are as therein defined:

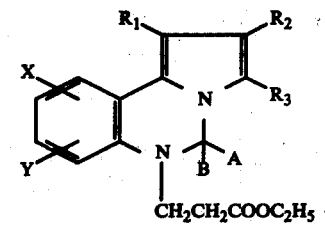

EXAMPLE XXV

Following the procedure of Example VII, but substituting for the 2-carbethoxy-5,6-dihydropyrrolo [1,2-c]quinazoline used therein an equivalent amount of each of the compounds produced in Examples XXII and XXIII, the corresponding compounds having the following general formula are produced, wherein X, Y, A, B, $R_1$, $R_2$, and $R_3$ are as therein defined:

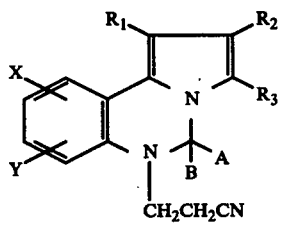

EXAMPLE XXVI

Following the procedure of Example IX, but substituting for the 2-carbethoxy-5,6-dihydropyrrolo [1,2-c]quinazoline used therein an equivalent amount of a compound produced in Examples XXII and XXIII, the corresponding compounds having the following general formula are produced, wherein X, Y, A, B, $R_1$, $R_2$, and $R_3$ are as defined in said Examples XXII and XXIII:

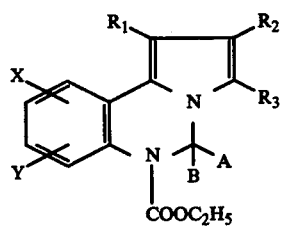

EXAMPLE XXVII

Following the procedure of Example X, but substituting for the 2-carbethoxy 5,6-dihydropyrrolo [1,2-c]quinazoline used therein an equivalent amount of a compound produced in Example XXII the corresponding compounds having the following general formula are produced, wherein X, Y, A, B, $R_1$, $R_2$, and $R_3$ are as defined in said Examples XXII and XXIII:

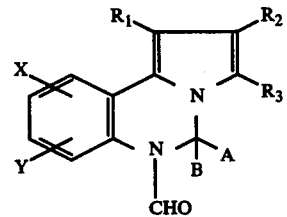

EXAMPLE XXVIII

Following the procedure of Example XI, but substituting for the 2-carbethoxy-5,6-dihydropyrrolo-6-formyl[1,2-c]-quinazoline used therein, an equivalent amount of a product of Example XXVII, the corresponding compounds having the following general formula are produced, wherein X, Y, A, B, $R_1$, $R_2$, and $R_3$ are as defined in said Example XXVII.

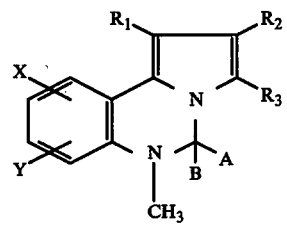

EXAMPLE XXIX

Following the procedure of Example XII, but substituting for the 2-carbethoxy-5,6-dihydropyrrolo-6-methyl[1,2-c]-quinazoline used therein an equivalent amount of the suitable reactant, the following products are obtained:

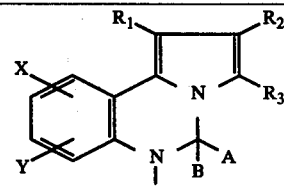

| X | Y | A | B | R1 | R2 | R3 | R4 |
|---|---|---|---|---|---|---|---|
| H | 7-OH | H | H | H | CH$_2$OH | H | H |
| H | 7-OCH$_3$ | H | H | H | CH$_2$OH | H | H |
| H | H | H | Cl | H | CH$_2$OH | H | H |
| H | H | H | OCH$_3$ | H | CH$_2$OH | H | H |
| H | H | H | N(CH$_3$)$_2$ | H | CH$_2$OH | H | H |
| 10-CH$_3$ | 7-CH$_3$ | H | CH$_3$ | H | CH$_2$OH | H | H |

EXAMPLE XXX

9-Bromo-2-carbethoxypyrrolo[1,2-c]-6[H]-4-quinazoliniumbromide:

A solution of ethyl bromopyruvate (78.0 g, 0.40 m) and 9-bromo-4-methylquinazoline (35.3 g, 0.16 m) in dry ethanol (1500 ml) was heated at reflux for 2 hr. The reaction mixture was concentrated to one-half volume, cooled, and a yellow solid formed. Filtration and drying yielded crude product as a yellow solid (30.45 g. m.p. 267°–268° C.). The filtrate was concentrated in vacuo to give a dark brown syrup. Trituration with CH$_2$Cl$_2$ yielded a yellow solid. Filtration and drying yielded additional product (9.61 g, m.p. 267°–268° C.). The combined products were washed well with CH$_2$Cl$_2$ and dried to yield the desired product as a yellow solid; m.p. 268°–270° C.

Anal. Calcd for C$_{14}$H$_{12}$Br$_2$N$_2$O$_2$: C, 42.04; H, 3.00; N, 7.00. Found: C, 42.06; H, 2.99; N, 6.83.

EXAMPLE XXXI

2-Carbethoxy-7-methoxypyrrolo[1,2-c]-6[H]-4-quinazolinium bromide

A solution of ethyl bromopyruvate (63.80 g, 0.327 m) and 8-methoxy-4-methylquinazoline (26.5 g, 0.168 m) in dry ethanol (1500 ml) was heated at reflux for 16 hr during which time a yellow precipitate formed. The reaction mixture was cooled and the solid filtered and dried to yield crude product. Treatment with charcoal and recrystallization from MeOH afforded the desired product as a yellow solid; m.p. 248°–249° C.

Anal. Calcd for $C_{15}H_{15}BrN_2O_3$: C, 51.32; H, 4.27; N, 7.98. Found: C, 51,52; H, 4.60; N, 7.67.

EXAMPLE XXXII

2-Carbethoxy-5-methylpyrrolo[1,2-c]-6-[H]-4-quinazolinium bromide

A solution of ethyl bromopyruvate (9.7 g, 0.050 m) and 2,4-dimethylquinazoline (7.0 g, 0.044 m) in dry EtOH (200 ml) was heated at reflux for 2 hr. During this time, a yellow solid formed. The reaction mixture was cooled and the yellow solid (6.7 g) was filtered. Crystallization from MeOH (800 ml) yielded a byproduct which was filtered off. Concentration of the filtrate yielded crude product. Recrystallization thereof from EtOH yielded the desired product as a yellow solid; m.p. 287°–289° C.

Anal. Calcd for $C_{15}H_{15}BrN_2O_2$: C, 53.74; H, 4.80; N, 8.32. Found: C, 54.06; H, 4.48; N, 8.22.

EXAMPLE XXXIII

3-Bromo-2-methylpyrrolo[1,2-c]quinazoline-[6H]-5-one hydrate

Bromine (1.6 g, 0.01 m) was added dropwise to a solution of the product of Example XVII (2.0 g, 0.01 m) in $CCl_4$ (600 ml) at reflux. The reaction mixture was refluxed for 1 hr and the solvent removed in vacuo to yield a dark solid residue (2.4 g). Trituration with MeOH (50 ml) and crystallization from benzene afforded the desired product as an off-white solid; m.p. >300°.

Anal. Calcd for $C_{12}H_9BrN_2O \cdot H_2O$: C, 48.86; H, 3.60; N, 9.48. Found: C, 49.17; H, 3.20; N, 9.14.

EXAMPLE XXXIV

2-Methyl-6-(β-carbethoxyethyl)pyrrolo[1,2-c]quinazolin-5-one

To a suspension of the product of Example XVII (3.0 g, 0.0151m) in ethyl acrylate (39 ml), cooled to 0°, was added dropwise Triton B (0.4 ml) over a 3 min period. An exothermic reaction resulted and a brown colored solution formed. The reaction mixture was refluxed for 6 hr. Excess ethyl acrylate was distilled in vacuo to yield a dark oil (4.6 g), which was crystallized from petroleum ether to afford the desired product, m.p. 74°–76°.

Anal. Calcd. for $C_{17}H_{18}N_2O_3$: C, 68.46 H, 6.04; N, 9.40. Found: C, 68.42; H, 6.18; N, 9.38.

EXAMPLE XXXV

2-Methyl-6-(β-carbomethoxyethyl)pyrrolo[1,2-c]quinazolin-5-one

Triton B (15 drops) was added dropwise over a 3 min period to a suspension of the product of Example XVII (7.0 g, 0.035 m) in methyl acrylate (140 ml), cooled to 0° C. Upon heating, all solids went into solution. The dark yellow reaction mixture was refluxed for 4 hr. Excess methyl acrylate was distilled in vacuo to yield a yellow oil that was crystallized from petroleum ether to afford the desired product; m.p. 89°–91°.

Anal. Calcd for $C_{16}H_{16}N_2O_3$: C, 67.59; H, 5.67; N, 9.85. Found: C, 67.23; H, 5.71; N, 9.77.

EXAMPLE XXXVI

2-Carbethoxy-5-methylpyrrolo[1,2-c]quinazoline

Sodium bicarbonate was added to a suspension of the product of Example XXXII (6.6 g, 0.02 m) in water (500 ml) until effervescence ceased. The aqueous mixture was then extracted several times with chloroform. The chloroform extracts were combined, dried ($Na_2SO_4$), filtered and the solvent removed in vacuo to yield a white solid (4.8 g). Crystallization from isopropanol (100 ml) - MeOH (30 ml) afforded the desired product as a white solid; m.p. 113°–116°.

Anal. Calcd for $C_{15}H_{14}N_2O_2$: C, 70.85; H, 5.55; N, 11.02. Found: C, 70.61; H, 5.77; N, 10.92.

EXAMPLE XXXVII 6-(3-Hydroxypropyl)-2-methyl-5,6-dihydropyrrolo[1,2-c]quinazoline $LiAlH_4$ (2.88 g, 0.076 m) was slurried in ether (250 ml) and to this was added a solution of the product of Example XXXV (5.5 g, 0.019 m) in ether (100 ml). The reaction mixture was stirred at ambient temperature for ½ hr. To the reaction mixture was added dropwise and successively $H_2O$ (3.0 ml), NaOH (3.0 ml of 15% aqueous), and $H_2O$ (9.0 ml). The resulting precipitate was filtered and washed with ether. The solvent was removed in vacuo from the filtrate and the residue crystallized from pentane to yield the desired product as a pale yellow solid; m.p. 77°–78° C.

Anal. Calcd for $C_{15}H_{18}N_2O$: C, 74.35; H, 7.49; N, 11.50. Found: C, 74.41; H, 7.72; N, 11.71.

EXAMPLE XXXVIII

2-Carbethoxy-5-methyl-5,6-dihydropyrrolo[1,2-c]quinazoline

The product of Example XXXVI (14.0 g, 0.0436 m) was dissolved in EtOH (1.5 lit) and the pH was adjusted to 4 with methanolic HCl. A solution of $NaBH_3CN$ (18.0 g, 0.272 m) in MeOH (300 ml) was added. The pH was readjusted to 4 at 5 min intervals for 20 min. After this time, the pH remained at 4. The reaction mixture was stirred at ambient temperature for 2 hr. The solvent was removed and the residue slurried in $H_2O$ (250 ml) and treated with 1N NaOH until basic. The mixture was extracted with $CH_2Cl_2$ (2 × 200 ml). The organic extract was dried over $Na_2SO_4$, filtered, and the solvent removed to give a white solid; m.p. 102°–103° C.

Anal. Calcd for $C_{15}H_{16}N_2O_2$: C, 70.29; H, 6.29; N, 10.93. Found: C, 70.27; H, 6.51; N, 10.83.

EXAMPLE XXXIX 2,6-Dicarbethoxy-5-methyl-5,6-dihydropyrrolo[1,2-c]quinazoline

A solution of the product of Example XXXVIII (3.0 g, 0.0117 m) and ethyl chloroformate (12.6 g, 0.117 m) in acetone (50 ml) and $H_2O$ (50 ml) was treated with NaOH (0.21 ml aq. 30%) and the mixture refluxed for 1 hr. The acetone was removed in vacuo and the aqueous residue cooled in ice-bath. A solid formed and this was filtered, washed with water, and dried in vacuo. The crude product (3.4 g) was crystallized from methanol (25 ml) to afford the desired product; m.p. 125°–127°.

Anal. Calcd for $C_{18}H_{20}N_2O_4$: C, 65.84; H, 6.14; N, 8.53. Found: C, 65.93; H, 5.92; N, 8.45.

EXAMPLE XL

9-Bromo-2-carbethoxypyrrolo[1,2-c]quinazoline

The product of Example XXX (4.0 g, 0.01 m) was slurried in $H_2O$ (100 ml), and $NaHCO_3$ was added until effervescence ceased. The aqueous mixture was extracted with $CH_2Cl_2$ (4 × 100ml). The organic extracts were combined, dried over Na$_2$SO$_4$, filtered, and the solvent removed in vacuo to yield an off-white solid (3.1 g). Recrystallization from EtOAc (after treatment with charcoal) afforded the desired product as a white solid; m.p. 183°–185° C.

Anal. Calcd for C$_{14}$H$_{11}$BrN$_2$O$_2$: C, 52.70; H, 3.44; H, 8.77. Found: C, 52.60; H, 3.45; N, 8.83.

EXAMPLE XLI

9-Bromo-2-carbethoxy-5,6-dihydropyrrolo[1,2-c]quinazoline

The product of Example XL (23.80 g 0.074m) was dissolved in MeOH (1000 ml) and the pH was adjusted to 4 with methanolic HCl. A solution of NaBH$_3$CN (27.40 g, 0.436 m) in MeOH (500 ml) was added. The pH was readjusted to 4 at 5 minute intervals for 20 min. After this time the pH remained at 4. The reaction mixture was stirred at room temperature for 2 hr. The solvent was removed and the residue slurried in H$_2$O (500 ml) and treated with 1N NaOH until basic. The mixture was extracted with CH$_2$Cl$_2$ (4 × 200 ml). The organic extracts were combined, dried over Na$_2$SO$_4$, filtered, and the solvent removed to give crude product as an off-white solid; 20.75 g; m.p. 169°–171° C. Crystallization from MeOH (after treatment with charcoal) afforded the desired product as a white solid; m.p. 170°–172°.

Anal. Calcd for C$_{14}$H$_{13}$BrN$_2$O$_2$: C, 52.37; H, 4.05; N, 8.72. Found: C, 52.02; H, 3.88; N, 8.58.

EXAMPLE XLII

2-Carbethoxy-7-methoxypyrrolo[1,2-c]quinazoline

The product of Example XXXI (34.50 g, 0.098 m) was slurried in H$_2$O, and NaHCO$_3$ was added until effervescence ceased. The aqueous mixture was extracted with CH$_2$Cl$_2$ (6 × 200 ml). The organic extracts were combined, dried over Na$_2$SO$_4$, filtered, and the solvent removed in vacuo to yield an off-white solid (26.27 g, m.p. = 153°–154° C.). Crystallization from MeOH (after treatment with charcoal) afforded the desired product as an off-white solid; m.p. 154°–155° C.

Anal. Calcd for C$_{15}$H$_{14}$N$_2$O$_3$: C, 66.66; H, 5.22; N, 10.36. Found: C, 67.05; H, 5.18; N, 10.36.

EXAMPLE XLIII

2-Hydroxymethyl-7-methoxy-5,6-dihydropyrrolo[1,2-c]quinazoline

LiAlH$_4$ (31.84 g, 0.84 m) was slurried in ether (2000 ml) and to this was added a solution of the product of Example XLII (15.17 g, 0.056 m) in ether (1000 ml). The reaction mixture was refluxed for 24 hrs and then cooled, and to it was added dropwise and successively, H$_2$O (32 ml), NaOH (32 ml of 15% aqueous) and H$_2$O (96 ml). The precipitate was filtered and washed with ether and CH$_2$Cl$_2$. The solvent was removed in vacuo from the filtrate to yield a pale greenish-white solid (11.35 g). Crystallization from MeOH afforded the desired product as a white solid; m.p. 137°–138° C.

Anal. Calcd for C$_{13}$H$_{14}$N$_2$O$_2$: C, 67.81; H, 6.13; N, 12.17. Found: C, 67.73; H, 6.13; N, 11.94.

EXAMPLE XLIV

2-Carbethoxy-7-methoxy-5,6-dihydropymmolo 1,2-c]quinazoline

The product of Example XXXI (5.0 g, 0.014 m) was dissolved in MeOH (450 ml) and the pH was adjusted to 4 with methanolic HCl. A solution of NaBH$_3$CN (3.58 g. 0.057 m) in MeOH (50 ml) was added. The original green colored solution turned brown. The pH was readjusted to 4 to 5 minute intervals for 20 minutes. After this time, the pH remained at 4. The reaction mixture was stirred at ambient temperature for 2 hrs. The solvent was removed and the residue slurried in H$_2$O (200 ml) and treated with 1M NaOH until basic. The mixture was extracted with ether (3 × 150 m) and CH$_2$Cl$_2$ (2 × 150 ml). The organic extracts were combined, dried over Na$_2$SO$_4$, filtered, and the solvent removed to give an off-white solid (3.72 g). Crystallizaton from MeOH (after treatment with charcoal) afforded the desired product as a white solid; m.p. 131°–133° C.

Anal. Calcd for C$_{15}$H$_{16}$N$_2$O$_3$: C, 66.16; H, 5.92; N, 10.29. Found: C, 65.84; H, 6.05; N, 10.21.

EXAMPLE XLV

2-Hydroxymethyl-6-(3-hydroxypropyl)-7-methoxy-5,6-dihydropyrrolo[1,2-c]quinazoline Triton B (25 drops) was added dropwise over a 3 min period to a suspension of the product of Example XLIV (9.3 g. 0.034 m) in methyl acrylate (300 ml). cooled at 0° C. Upon heating, all solids when into solution. The reaction mixture was refluxed for 3 hours. Excess methyl acrylate was then removed by distillation in vacuo to yield a dark brown syrup (12.19 g). LiAlH$_4$ (12.89 g, 0.34 m) was slurried in ether (500 ml) and to this was added dropwise a solution of the above dark brown syrup in ether (500 ml). The reaction mixture was stirred at ambient temperature for 0.5 hr. To the reaction mixture was added dropwise and successively, H$_2$O (13.0 ml), NaOH (13.0 ml of 15% aqueous) and H$_2$O (39.0 ml). The precipitate was filtered and washed well with CH$_2$Cl$_2$. Removal of the solvent from the filtrate yielded a colorless oil, 9.80 g. Cyrstallization of the oil from either yielded the desired product as a white solid; m.p. 116°–118° C.

Anal. Calcd for C$_{16}$H$_{20}$N$_2$O$_3$: C, 66.65; H, 6.99; N, 9.72. Found: C, 66.42; H, 7.26; N, 9.63.

EXAMPLE XLVI

2-Carbethoxy-6-($\beta$-cyanoethyl)-7-methoxy-5,6-dihydropyrrolo[1,2-c]quinazoline The product of Example XLIV (4.5 g, 0.016 m) was suspended in CH$_3$CN (90 ml) and acrylonitrile (freshly distilled, 45 ml). The mixture was cooled to 0°–5° C. and Triton B (20 drops) was added dropwise. The original green mixture turned brown and all solids went into solution. The reaction mixture was refluxed for 3 hr. Removal of the solvent in vacuo yielded a drak brown syrup (3.1 g). Treatment of the syrup with charcoal, followed by crystallization from MeOH (3X) afforded the desired product as a white solid; m.p. 146°–147° C.

Anal. Calcd for C$_{18}$H$_{19}$N$_3$O$_3$: C, 66.45; H, 5.89; N, 12.21. Found: C, 66.04; H, 5.96; N, 13.09.

EXAMPLE XLVII

9-Bromo-2,6-dicarbethoxy-5,6-dihydropyrrolo[1,2-c]quinazoline

A solution of the product of Example XLI (5.0 g, 0.015 m) and ethyl chloroformate (16.30 g, 0.15 m) in acetone (300 ml) and H$_2$O (170 ml) was treated with NaOH (0.5 ml of 30% aqueous) and heated at reflux for 1 hr. The acetone was removed in vacuo and the aqueous residue cooled in an ice-bath. An off-white solid formed and this was filtered, washed with H$_2$O, and dried. Recrystallization from MeOH (after treatment with charcoal) yielded the desired product as a white solid; 4.44 g, mp = 161°–163° C.

Anal. Calcd for $C_{17}H_{17}BrN_2O_4$: C, 51.94; H, 4.32; N, 7.12. Found: C, 51.98; H, 4.29; N, 7.11.

EXAMPLE XLVIII 2,6-Dicarbethoxy-7-methoxy-5,6-dihydropyrrolo[1,2-c]quinazoline A solution of the product of Example XLIV (4.40 g, 0.016 m) and ethyl chloroformate (17.36 g, 0.16 m) in acetone (250 ml) and $H_2O$ (150 ml) was treated with NaOH (0.3 ml of 30% aqueous) and the mixture was refluxed for 2 hr. The acetone was removed in vacuo and the aqueous residue cooled in an ice-bath. An off-white solid formed and was filtered and dried. Recrystallization from MeOH (after treatment with charcoal) afforded the desired prod-product as a white solid; 4.07 g, mp = 172°–174° C.

Anal. Calcd for $C_{18}H_{20}N_2O_5$: C, 62.78; H, 5.85; N, 8.13. Found: C, 62.44; H, 5.76; N, 8.02.

EXAMPLE XLIX

2-Carbethoxy-9-cyanopyrrolo[1,2-c]quinazoline

The product of Example XLI (6.90 g, 0.021 m) and copper cyanide (7.73 g, 0.086 m) in DMF (500 ml) were heated at reflux for 16 hours. The dark brown reaction mixture was cooled and then poured into conc $NH_4OH$ (276 ml). The resulting mixture was extracted with $CH_2Cl_2$ (1800 ml) and the extract was washed with 2N HCl (3 × 150 ml) and $H_2O$ (3 × 150 ml) and dried over $Na_2SO_4$. Removal of the solvent in vacuo yielded a light brown semi-solid (4.55 g). The crude product was chromatographed on a 400 g SilicAR column (50 mm i.d. + 30 cm long) prepared in benzene. Elution with 2–4% EtOAc/benzene removed a byproduct, and elution with 4% EtOAc/benzene afforded the desired product, 2-carbethoxy-9-cyanopyrrolo[1,2-c]quinazoline; m.p. 264°–266° C.

Anal. Calcd for $C_{15}H_{11}N_3O_2$: C, 67.92; H, 4.18; N, 15.84. Found: C, 68.18; H, 4.51; N, 15.56.

EXAMPLE L

2-Carbethoxy-9-cyano-5,6-dihydropyrrolo[1,2-c]quinazoline

Continued elution of the crude product of Example XLIX with 6–8% EtOH/benzene yielded the desired product, 2-carbethoxy-9-cyano-5,6-dihydropyrrolo[1,2-c]quinazoline; m.p. 228°–230° C.

Anal. Calcd for $C_{15}H_{13}N_3O_2$: C, 67.41; H, 4.90; N, 15.72. Found: C, 67.42; H, 5.21; N, 15.63.

The above examples have been provided by way of illustration and not to limit the scope of the present invention, which scope is defined by the appended claims.

What is claimed is:

1. A substituted pyrrolo(1,2-c)quinazoline of the formula:

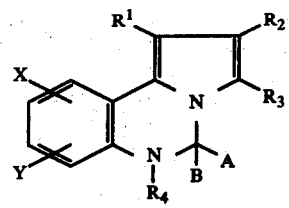

and pharmaceutically-acceptable acid addition salts thereof, wherein:

$R_1$ and $R_2$ are each members selected from the group consisting of hydrogen, loweralkyl, naphthyl, phenyl, halophenyl, loweralkyphenyl, loweralkoxyphenyl, amino, COOH, COO loweralkyl;

$R_3$ is a member selected from the group consisting of hydrogen, loweralkyl, loweralkenyl, and haloloweralkenyl;

$R_4$ is a member selected from the group consisting of hydrogen, hydroxymethyl, loweralkyl, cyanoethyl, CHO, COOH, COO loweralkyl, $(CH_2)_2COOH$, $(CH_2)_2COO$ loweralkyl, X and Y are each members selected from the group consisting of hydrogen, halo, loweralkoxy, cyano;

a considered separately is hydrogen;

B considered separately is a member selected from the group consisting of hydrogen, halo; and A and B considered together is a member selected from the group consisting of oxygen and sulfur.

2. The substituted pyrrole[1,2-c]quinazoline of claim 1 having the formula:

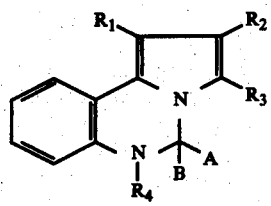

and pharmaceutically-acceptable acid addition salts thereof, wherein:

$R_1$ is a member selected from the group consisting of hydrogen and COO loweralkyl;

$R_2$ is a member selected from the group consisting of hydrogen, loweralkyl, hydroxymethyl, and COO loweralkyl;

$R_3$ is a member selected from the group consisting of hydrogen, halo, loweralkyl, loweralkenyl, and halosubstituted loweralkenyl;

$R_4$ is a member selected from the group consisting of hydrogen, loweralkyl, hydroxyloweralkyl, cyanoethyl, CHO, COO loweralkyl, $CH_2CH_2COO$ loweralkyl, and $CH_2CH_2COOH$;

A considered separately is hydrogen;

B considered separately is a member selected from the group consisting of hydrogen and loweralkyl; and A and B considered together is oxygen.

3. The substituted pyrrolo[1,2-c]quinazoline of claim 1 having the formula:

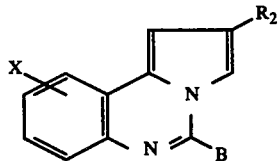

and pharmaceutically-acceptable acid addition salts thereof, wherein X is a member selected from the group consisting of hydrogen, halo, loweralkoxy, and cyano; B is a member selected from the group consisting of hydrogen and loweralkyl; and $R_2$ is a member selected from the group consisting of COOH and COO loweralkyl.

4. The compound of claim 2 that is selected from the group consisting of 2-carbethoxy, 5,6-dihydropyrrolo-[1,2-c]quinazoline and the pharmaceutically-acceptable acid addition salts thereof.

5. The compound of claim 2 that is a member selected from the group consisting of 2-carbethoxy-5,6-dihydropyrrolo[1,2-c]quinazoline-6-propionitrile and the pharmaceutically-acceptable acid addition salts thereof.

6. The compound of claim 2 that is a member selected from the group consisting of 2,6-dicarbethoxy-5,6-dihydropyrrolo[1,2-c]quinazoline and the pharmaceutically-acceptable acid addition salts thereof.

7. The compound of claim 2 that is a member selected from the group consisting of 2-carbethoxy-5,6-dihydropyrrolo-6-formyl[1,2-c]quinazoline and the pharmaceutically-acceptable acid addition salts thereof.

8. The compound of claim 2 that is a member selected from the group consisting of 2-carbethoxy-5,6-dihydropyrrolo-6-methyl[1,2-c]quinazoline and the pharmaceutically-acceptable acid addition salts thereof.

9. The compound of claim 2 that is a member selected from the group consisting of 2-hydroxymethyl-6-methyl-5,6-dihydropyrrolo[1,2-c]quinazoline and the pharmaceutically-acceptable acid addition salts thereof.

10. The compound of claim 2 that is a member selected from the group consisting of 2-carbethoxy-6-(β-cyanoethyl)pyrrolo-[1,2-c]quinazolin-6[H]-5-one and the pharmaceutically-acceptable acid addition salts thereof.

11. The compound of claim 2 that is a member selected from the group consisting of 2-methylpyrrolo[1,2-c]quinazolin-6[H]-5-one and the pharmaceutically-acceptable acid addition salts thereof.

12. The compound of claim 2 that is a member selected from the group consisting of 3-methylpyrrolo[1,2-c]quinazolin-6[H]-5-one and the pharmaceutically-acceptable acid addition salts thereof.

13. The compound of claim 2 that is a member selected from the group consisting of 2-methyl-6-(β-cyanoethyl)-pyrrolo[1,2-c]quinazolin-6[H]-5-one and the pharmaceutically-acceptable acid addition salts thereof.

14. The compound of claim 2 that is a member selected from the group consisting of 3-bromo-2-methyl-pyrrolo[1,2-c]quinazolin-6[H]-5-one and the pharmaceutically-acceptable acid addition salts thereof.

15. The compound of claim 2 that is a member selected from the group consisting of 2-carbethoxy-5-methyl-5,6-dihydropyrrolo[1,2-c]quinazoline and the pharmaceutically acceptable acid addition salts thereof.

16. The compound of claim 2 that is a member selected from the group consisting of 2,6-dicarbethoxy-5-methyl-5,6-dihydropyrrolo[1,2-c]quinazoline and the pharmaceutically-acceptable acid addition salts thereof.

17. The compound of claim 2 that is a member selected from the group consisting of 2-carbethoxy-6-(β-cyanoethyl)-7-methoxy-5,6-dihydropyrrolo[1,2-c]quinazoline and the pharmaceutically-acceptable acid addition salts thereof.

18. The compound of claim 3 that is a member selected from the group consisting of 2-carbethoxypyrrolo[1,2-c]quinazoline and the pharmaceutically-acceptable acid addition salts thereof.

19. The compound of claim 3 that is a member selected from the group consisting of pyrrolo[1,2-c]quinazoline-2-carboxylic acid and the pharmaceutically-acceptable acid addition salts thereof.

20. The compound of claim 3 that is a member selected from the group consisting of 2-carbethoxy-5-methylpyrrolo[1,2-c]quinazoline and the pharmaceutically-acceptable acid addition salts thereof.

21. The compound of claim 3 that is a member selected from the group consisting of 2-carbethoxy-9-cyanopyrrolo[1,2-c]-quinazoline and the pharmaceutically-acceptable acid addition salts thereof.

22. A pharmaceutical composition useful in the treatment of cardiovascular disorders in dosage unit form comprising per dosage unit from about 5 to about 500 mg. of a compound of claim 1 in admixture with a pharmaceutical carrier suitable for internal administration.

23. The method of treating a patient having hypertension which comprises systemically administering to said patient an effective anti-hypertensive amount of a compound of claim 1.

24. The method of treating a patient having bradycardia which comprises systemically administering to said pateint an effective anti-bradycardia amount of a compound of claim 1.

25. The method of treating a patient having cardiac arrythmia which comprises systemically administering to said patient an effective anti-arrythmia amount of a compound of claim 1.

26. The method of treating a patient having asthma which comprises systemically administering to said patient an effective anti-asthma amount of a compound of claim 1.

27. A substituted pyrrolo[1,2-c]quinazoline of the formula:

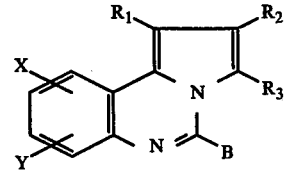

and pharmaceutically-acceptable acid addition salts thereof, wherein:

$R_1$ and $R_2$ are each members selected from the group consisting of hydrogen, loweralkyl, naphthyl, phenyl, halophenyl, loweralkylphenyl, loweralkoxyphenyl, amino, COOH, COO loweralkyl;

$R_3$ is a member selected from the group consisting of hydrogen, loweralkenyl, and haloloweralkenyl;

X and Y are each members selected from the group consisting of hydrogen, halo, loweralkoxy, cyano;

B considered separately is a member selected from the group consisting of hydrogen and halo.

28. The process for the preparation of a substituted pyrrolo[1,2-c]quinazoline of the formula

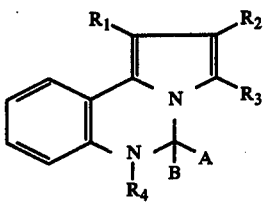

which comprises reacting in a suitable cyclization solvent a substituted quinazoline of the formula

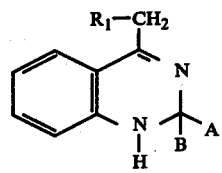

with a halo compound of the formula

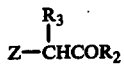

wherein $R_1$ is a member selected from the group consisting of hydrogen and COO loweralkyl;

$R_2$ is a member selected from the group consisting of hydrogen, loweralkyl, hydroxymethyl, and COO loweralkyl;

$R_3$ is a member selected from the group consisting of hydrogen, halo, loweralkyl, loweralkenyl, and halosubstituted loweralkenyl;

$R_4$ is a member selected from the group consisting of hydrogen, loweralkyl, hydroxyloweralkyl, cyanoethyl, CHO, COO loweralkyl, $CH_2CH_2COO$ loweralkyl, and $CH_2CH_2COOH$;

A considered separately is hydrogen;

B considered separately is a member selected from the group consisting of hydrogen and loweralkyl;

A and B considered together is oxygen; and

Z is a member selected from the group consisting of chloro and bromo.

29. The process for the preparation of a substituted pyrrolo[1,2-c]quinazoline of the formula

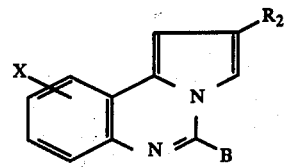

which comprises reacting in a suitable cyclization solvent a substituted quinazoline of the formula

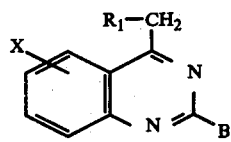

with a halo compound of the formula

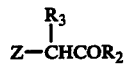

wherein

X is a member selected from the group consisting of hydrogen, halo, loweralkoxy and cyano; B is a member selected from the group consisting of hydrogen and loweralkyl;

$R_1$ is a member selected from the group consisting of hydrogen and COO loweralkyl;

$R_2$ is a member selected from the group consisting of COOH and COO loweralkyl;

$R_3$ is a member selected from the group consisting of hydrogen, halo, loweralkyl, loweralkenyl, and halosubstituted loweralkenyl; and Z is a member selected from the group consisting of chloro and bromo.

* * * * *

UNITED STATES PATENT AND TRADEMARK OFFICE
CERTIFICATE OF CORRECTION

PATENT NO. : 4,129,653  
DATED : December 12, 1978  
INVENTOR(S) : Victor T. Bandurco, Seymour Levine It is certified that error appears in the above-identified patent and that said Letters Patent are hereby corrected as shown below:

At Column 10, Table I, Reagent/Reaction Column, Lines 6 and 15, "reduction (LiALH$_4$ or diborane)" should be
-- reduction (LiAlH$_4$ or diborane) --.

At Column 13, Line 32, "C, 69.14" should be -- C, 69.41 --.
At Column 16, Line 5, "was CHCl$_3$" should be -- with CHCl$_3$ --.
At Column 18 and continued at Column 19, Example XXII, formula is incorrect

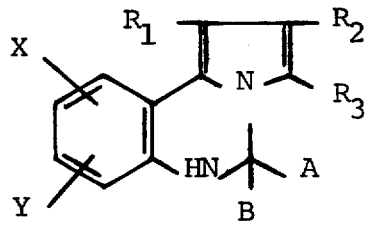     should be --     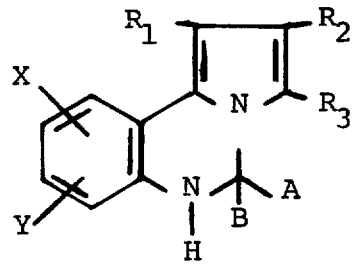     --

At Column 19, Example XXII (Chart Col. X, Line 9), "10-C$_6$H" should be -- 10-C$_6$H$_5$ --.
At Column 20, Example XXIII (Chart Col. AB, Line 2), "0" should be -- O --.
At Column 23, Line 2, "C, 51,52" should be -- C, 51.52 --.
At Column 25, Line 63, Example XLIV, in the Title, "5,6-dihydropymmolo" should be -- 5,6-dihydropyrrolo --.
At Column 26, Line 3, "to 4 to 5 minute" should be -- to 4 at 5 minute --.

UNITED STATES PATENT AND TRADEMARK OFFICE
CERTIFICATE OF CORRECTION

PATENT NO. : 4,129,653
DATED : December 12, 1978
INVENTOR(S) : Victor T. Bandurco, Seymour Levine It is certified that error appears in the above-identified patent and that said Letters Patent are hereby corrected as shown below:

At Column 26, Line 23, "(300 ml)." should be -- (300 ml), --.
At Column 26, Line 24, "when into solution" should be
  -- went into solution --.
At Column 26, Line 57, "12.21" should be -- 12.91 --.
At Columns 7 and 8, the formulas which appear at the top of
  each column run into each other and should be as follows:
At Column 7, Lines 1-20

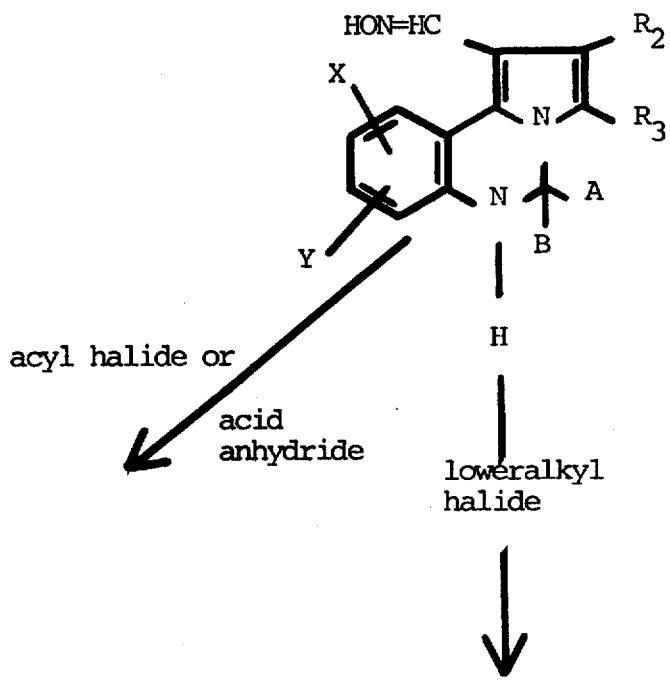

UNITED STATES PATENT AND TRADEMARK OFFICE
CERTIFICATE OF CORRECTION

PATENT NO. : 4,129,653

DATED : December 12, 1978

INVENTOR(S) : Victor T. Bandurco, Seymour Levine

It is certified that error appears in the above-identified patent and that said Letters Patent are hereby corrected as shown below:

At Column 8, Lines 1-9 should be

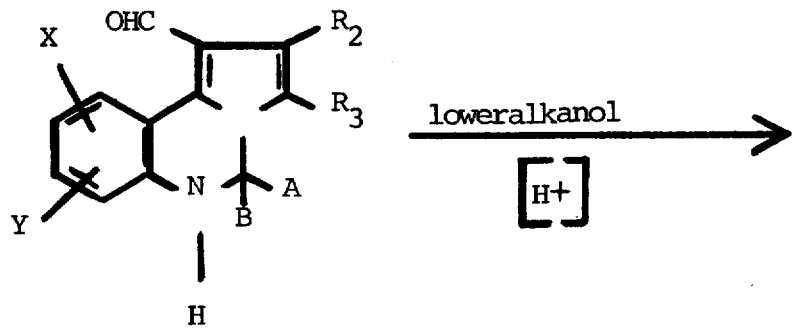

Signed and Sealed this

Tenth Day of April 1979

[SEAL]

Attest:

RUTH C. MASON
*Attesting Officer*

DONALD W. BANNER
*Commissioner of Patents and Trademarks*